United States Patent [19]

Johnston et al.

[11] Patent Number: 4,783,443
[45] Date of Patent: Nov. 8, 1988

[54] AMINO ACYL CEPHALOSPORIN DERIVATIVES

[75] Inventors: Michael A. Johnston; Shahrair Mobashery, both of Chicago, Ill.

[73] Assignee: The University of Chicago, Chicago, Ill.

[21] Appl. No.: 835,280

[22] Filed: Mar. 3, 1986

[51] Int. Cl.$^4$ .................. C07D 501/46; A61K 31/545
[52] U.S. Cl. ........................................ 514/19; 514/18; 514/202; 530/330; 530/331; 540/222
[58] Field of Search ................. 540/228, 222; 514/202, 514/18, 19; 530/330, 331

[56] References Cited

U.S. PATENT DOCUMENTS

| | | | |
|---|---|---|---|
| 3,624,225 | 11/1971 | O'Callaghan | 540/225 |
| 4,237,128 | 12/1980 | Cimarusti et al. | 540/228 |
| 4,285,939 | 8/1981 | Machida et al. | 540/228 |
| 4,301,161 | 11/1981 | Oi et al. | 540/226 |
| 4,386,199 | 5/1983 | Treuner et al. | 540/228 |
| 4,501,741 | 2/1985 | Graves et al. | 514/202 |
| 4,637,999 | 1/1987 | Doherty et al. | 514/201 |

FOREIGN PATENT DOCUMENTS 0124081 7/1984 European Pat. Off. .
0127543 12/1984 European Pat. Off. .
1333905 10/1973 United Kingdom .

OTHER PUBLICATIONS

David Berges, J. Med. Chem., 1975, vol. 18, 1264–1265.
Mobashery et al., J. Biol. Chem., 1986, vol. 261, 7879–7887.
Mobashery et al., J. Am. Chem. Soc., 1986, vol. 108, 1685–1686.
Chemical Abstracts, vol. 102, (1985): 184902z.
Doyle et al., Adv. Drug. Res., 1:1, (1964).
Nagarajan et al., J. Amer. Chem. Soc., 93:2308, (1971).
Kahan et al., J. Antibiot., 32:1, (1974).
Komatsu, Antimicrob. Agents Chemother., 17:316, (1980).
Sykes et al., Antimicrob. Agents Chemother., 21:85, (1982).
Brown, J. Antibiot., 29:668, (1976).
Brown, J. Chem. Soc. Chem. Comm., (1977), 523.
English, Antimicrob. Agents Chemother., 14:414, (1978).
Pratt, PNAS, 75:4145, (1978).
Wright et al., J. Antibiot., 32:1155, (1979).
Wheeler et al., J. Med. Chem., 20:1159, (1977).
Wheeler et al., J. Med. Chem., 22:657, (1979).
Binderup et al., J. Antibiot., 24:767, (1971).
Sassiver et al., "Structure–Activity Relationships among the Semisynthetic Antibiotics", (Perlman, D., ed), New York: Academic Press, 1977, pp. 87–160.
Weber et al., ibid, pp. 161–237.
Chauvette et al., J. Amer. Chem. Soc., 84:3401, (1962).
Soper et al., J. Biol. Chem., 252:3170–3175, (1977).
Kollonitsch et al., Nature, 243:346–347, (1973).
Kollonitsch et al., J. Am. Chem. Soc., 98:5591–5593, (1976).
Wang et al., Biochemistry, 17:1313–1321, (1978).
Wang et al., Biochemistry, 20:7539–7546, (1981).
Badet et al., Biochemistry, 23:5188–5194, (1984).
Rosie et al., Biochemistry, 23:5195–5201, (1984).
Cheung, K.-S. et al., J. Med. Chem., 26:1733–1741, (1983).

Primary Examiner—Nicholas S. Rizzo
Attorney, Agent, or Firm—Saidman, Sterne, Kessler & Goldstein

[57] ABSTRACT

Antibacterial cephalosporin compounds of the Formula (I):

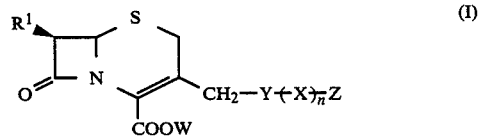

wherein W is a pharmaceutically acceptable salt or a carboxyl-protecting group; n is an integer from 1 to 2; —X— is —$X^1$— where the $X^1$ moieties are the same or different and selected from the group consisting of (D) or (L)

(Abstract continued on next page.)

Y is —O—; wherein R¹ is selected from the group consisting of:

$R^2$ is H, —CH$_2$R$^4$, —CHR$^5_2$ or —CR$^5_3$, wherein R$^4$ is H, F, Cl, Br, —OH, —CN,

—CH(CH$_3$)$_2$, —CH$_2$(OH), or —C≡CH, where Q$^1$, Q$^2$ and Q$^3$ are the same or different and selected from the group consisting of H, F, Cl or Br; R$^5$ is F, Cl or Br; and Z$^1$ is H or an amino protecting group.

11 Claims, 2 Drawing Sheets

AMINO ACYL CEPHALOSPORIN DERIVATIVES

FIELD OF THE INVENTION

The present invention relates to cephalosporin derivatives which bear a $C_{10}$-amino acid, peptidyl substituent, or derivatives of the amino acid or peptidyl substituent. These compounds are antibacterial agents, including in several instances, with activity against beta-lactam antibiotic-resistant strains.

DESCRIPTION OF THE BACKGROUND ART

Resistance within a bacterial population to the beta-lactam antibiotics results in part from the widespread presence of beta-lactamase enzymes in bacteria, including in human pathogens. These enzymes catalyze the hydrolysis of the beta-lactam ring of both penicillins and cephalosporins; the products of fragmentation lack antibiotic activity. The development of resistance to the beta-lactam antibiotics remains an important clinical problem.

The problem has been traditionally addressed by strategies chiefly designed to circumvent it. Considerable attention, for example, has been given to the development of new beta-lactams with improved lactamase stability. These include the penems (Doyle, F. P. et al., Adv. Drug. Res. 1:1, 1964), the cephamycins (Nagarajan, R. et al., J. Amer. Chem. Soc., 93:2308 (1971)), thienamycin (Komatsu, Y., Antimicrob. Agents Chemother., 17:316 (1980), and Kahan, J. S., et al., J. Antibiot. 32:1 (1974), and the monobactams (Sykes, R. et al. ibid. 21:85 (1982)). An alternate approach centers on the possibility of co-administration of a beta-lactam and a lactamase inhibitor, such as clavulanic acid (Brown, A. G., J. Antibiot. 29:668 (1976)), a carbapenem (Brown, A. G., J. Chem. Soc. Chem. Comm. (1977), 523), a penicillinate sulfone (English, A. R., Antimicrob. Agents Chemother. 14:414 (1978)) or a 6-halopenem (Pratt, R. S., Proc. Natl. Acad. Sci. USA 75:4145 (1978)).

In spite of these efforts, and continuing research in this field, a need still exists for improved and powerful antibacterials with a wide bacterial profile, and especially those which are capable of inhibiting or blocking the growth of beta-lactam antibioticresistant strains.

SUMMARY OF THE INVENTION

The present invention provides a novel family of cephalosporin-based antibiotic compounds. The compounds are those of the following Formula (I):

$$\text{(I)}$$

wherein

W is a pharmaceutically acceptable salt or a carboxyl-protecting group; n is an intgeger from 0 to 5;
—X— is —$X^1$— or —$X^2$— where
the $X^1$ moieties are the same or different and selected from the group consisting of (D) or (L)

$$-\underset{\underset{O}{\parallel}}{C}-\underset{\underset{R^2}{|}}{CH}-NH-,$$

and
the —$X^2$— moieties are the same or different and selected from the group consisting of (D) or (L)

$$-NH-\underset{\underset{R^2}{|}}{CH}-\underset{\underset{O}{\parallel}}{C}-;$$

with the proviso that
(a) when X is $X^1$, n is an integer from 1 to 5, Z is $Z^1$, and Y is either —O— or $$-Y^1-\underset{\underset{R^3}{|}}{CH}-\underset{\underset{COZ^2}{|}}{CH}-NH-,$$

(b) when X is $X^2$, n is an integer from 1 to 5, Z is $Z^2$, and Y is either $$-O-\underset{\underset{O}{\parallel}}{C}- \text{ or } -Y^1-\underset{\underset{R^3}{|}}{CH}-\underset{\underset{NHZ^1}{|}}{CH}-\underset{\underset{O}{\parallel}}{C}- \text{ and}$$

(c) when n is O, Y is $$-Y^1-\underset{\underset{R^3}{|}}{CH}-\underset{\underset{COZ^2}{|}}{CH}-NHZ^1;$$

wherein $R^1$ is a functional group which does not substantially prevent hydrolysis of the cephalosphorin by endogenous bacterial enzymes,
$Y^1$ is —O— or —S—;
$R^2$ is H, —$CH_2R^4$, —$CHR^5_2$ or —$CR^5_3$
where $R^4$ is H, F, Cl, Br, —OH, —CN, $$-O\underset{\underset{O}{\parallel}}{C}(\underset{\underset{Q^3}{|}}{\overset{Q^1}{|}})-Q^2, -CH(CH_3)_2, -CH(OH),$$

$$-O-\underset{\underset{O}{\parallel}}{C}-NH_2, \text{ or } -C\equiv CH;$$

$Q^1$, $Q^2$ and $Q^3$ are the same or different and selected from the group consisting of H, F, Cl or Br;
$R^5$ is F, Cl or Br;
$R^3$ is H or —$CH_3$;
$Z^1$ is H or an amino protecting group; and
$Z^2$ is $OR^6$ or —$NR^7R^8$
where $R^6$ is H, a pharmaceutically acceptable cation or a pharmaceutically acceptable ester,
$R^7$ and $R^8$ are the same or different and selected from the group consisting of H or lower alkyl, or wherein $R^7$ and $R^8$ together with the nitrogen atom form a heterocyclic ring.

The compounds are broad spectrum antibacterial agents with activity against both Gram positive and Gram negative species, including, in many instances, strains that display widespread resistance to conventional beta-lactam antibiotics, such as certain E. coli strains, H. influenzae, Corynebacterium strains, and penicillin- and methicillin-resistant strains of *Staphylococcus aureus* and *S. epidermidis*.

The invention also relates to processes for preparing these compounds, intermediates utilized during the preparation—which are useful as such or may find use as antibiotics by themselves—pharmaceutical compositions comprising the compounds, as well as uses of the compounds in antibacterial treatment.

DESCRIPTION OF THE PREFERRED EMBODIMENTS

The compounds of the invention are those having Formula I, above. They are cephalosporins which bear aminoacyl or peptidyl substituents at the $C_{10}$-position.

The compounds all share the 3-cephem-4-carboxylate nucleus, or pharmacologically acceptable salts thereof. The cephem must contain $\Delta^3$-unsaturation; $\Delta^2$-cephems are not acceptable.

The beta-lactam ring may not have a 7-alpha-substituent as $R^1$. However, a 7-beta $R^1$ substituent may be any of the number of side chains known in the prior art which do not block, prevent or reduce the reactivity of the cephalosporin towards enzymatic hydrolysis by endogenous bacterial enzymes, such as lactamases or penicillinases. In addition, the $R^1$ substituent should not substantially compromises the ability of the cephalosporin to react with Penicillin Binding Proteins (PBPs).

$R^1$ is normally an amide. Acceptable $R^1$ substituents are:

(a) Aromatic aminoacyls such as where $R^9$ is H, Cl or OH, and $R^{10}$ is H or OH;

(b) Phenoxyacetyl or phenylthioacetyl, such as where $Y^1$ is as indicated previously, and $R^{11}$ is H, p-Br, p-Cl, o-Cl, o-$N_2$, m-F or lower ($C_1$-$C_6$) alkyl, or lower ($C_1$-$C_6$) acyl;

(c) Alpha-substituted or unsubstituted aromatic acetyls, such as where $R^{12}$ is H, —$CH_3$, Cl, Br, —$OCH_3$, —$SCH_3$, acetyl, and the like;

(d) Non-armatic aminoacyls, such as:

and
(e) Fused-ring acyls, such as:

For reference to the known aforementioned $R^1$ substituents see, for example, Sassiver, M. L. et al., in *Structure-Activity Relationships among the Semisynthetic Antiobiotics*, (Perlman, D., ed), New York, Academic Press, 1977, p. 87–160; Weber, J. A., ibid, p 161–237, and references therein, all herein incorporated by references.

The integer n can be from 0 to 5, the only characteristic being that the peptidyl side chain not become too long, so as to be unreactive with, or nonbinding to, beta-lactamase or penicillin binding proteins. Preferably n is from 1 to 5, most preferably 1–3. Specifically noted values ar n=1 or n=2.

X in Formula I is an amino acid, a derivative of an amino acid, a peptidyl or a derivative of a peptidyl group. X is bound to the cephalosporin ring through moiety Y, at position C-10.

When X is $X^1$, Y is either —O— or an amino acid group derived from serine ($Y^1$=O; $R^3$=H), threonine ($Y^1$=O; $R^3$=CH$_3$), cysteine ($Y^1$=S; $R^3$=H), or the thio derivative of threonine ($Y^1$=S; $R^3$=CH$_3$). This amino acid group is bound to $X^1$ through its amino function. When X is $X^1$, n is an integer from 1 to 5.

When X is $X^2$, Y is either carbonate linkage or an amino acid group, as above, derived from serine, threonine, cysteine, or the thio-derivative of threonine. In this case, this amino acid group is bound to $X^2$ through its carboxyl function instead, i.e. the orientation is backwards from the situation where X is $X^1$. When X is $X^2$, n is an integer from 1 to 5.

When n is greater than 1, the —X— moieties may be the same or different. The —X— moieties can either be in the D configuration or L configuration.

When n is zero, the cephalosporin carries at C-10 a residue which is a serine, threonine, cysteine or thio derivative of threonine, bound through —O— or —S—.

Among specific amino acid moieties included in —X— are glycine, alanine, valine, serine, threonine, carbamoyl-O-serine, propargylglycine, beta-chloroalanine, beta-fluoroalanine, beta-cyanoalanine, beta, beta-dichloroalanine, trichloroalanine, trifluoroalanine or haloacetyl-O-serine.

Among the preferred amino acid moieties —X— are derivatives of alanine, carrying at the beta position thereof a halo or multihalo substituent, or a cyano, carbamoyl or —C≡CH substituent.

Most preferred among the —X— moieties are those carrying beta-haloalanine substituents, such as beta-chloroalanine. Especially noted among those, are haloalanyl residues where n is greater than 1.

The terminal or outermost X moiety of an aminoacyl or peptidyl chain may end in a free amino group ($Z^2$ is hydrogen) or in an amino protecting group ($Z^2$ is an amino protecting group).

Alternatively, depending on the orientation of the aminoacyl or peptidyl substituuent at C-10, the end group is an ester, free acid or salt (OR$^6$), or an acyclic or cyclic amide (—NR$^7$R$^8$).

Among protecting groups useful for the amino functions are well known ones, such as tert-butyloxycarbonyl benzyloxycarbonyl, acetyl, trifluoroacetyl, formyl, toluenesulfonyl, and the like.

Cyclic amides include piperidine, pyrrolidine, morpholine, piperazine, and the like.

The compounds may be present in their pharmacologically or pharmaceutically acceptable salts or esters. The salts can be cationic salts formed at the carboxyl group at C-9, or at any other carboxyl group, or anionic salts formed at any amino function, e.g., at the terminus of the peptidyl residue. Alternatively, the compounds are in their zwitterionic forms.

Among preferred anionic counterions are those of the halides (derived from the hydrohalic acids), such as chloride, bromide, or fluoride. Other anions are sulfonate, or p-toluenesulfonate.

Pharmaceutically acceptable cationic salts useful for the purposes of this invention are, for example, pharmaceutically acceptable metal salts or amine salts.

Especially preferred metal salts are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmaceutically acceptable amine salts are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, alphaphenylethylamine, beta-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methyl-pyrrolidine, 1,4-dimethylpiperazine, 2-methylpiperidine, and the like, as well as amines containing water-solubilizing or hydrophilic groups, e.g., mono-, di, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)dimethylglucosamine, ephedrine, phenylephedrine, epinephrine, procaine, and the like.

Examples of suitable pharmaceutically acceptable quaternary ammonium salts are tetramethylammonium, tetraethylammonium, benzyltrimethylammonium, phenyltriethylammonium, and the like.

Pharmaceutically acceptable radicals W (at C-9) include lower ($C_1$–$C_6$) straight or branched chain alkyl groups, or radicals known to render the resulting cephem ester orally active. Among such W radicals are:

(a) Acetoxymethyl (—CH$_2$—O—CO—CH$_3$) (see Wright et al *J. Antibiot.* 32: 1155 (1979), Wheeler, W. J. at al, *J. Med. Chem.* 20: 1159 (1977));

(b) Aminoacyloxymethyl, such as:

where m is an integer whihh is 0 or 1, and R$^{13}$ is —CH(CH$_3$)$_2$, —CH$_2$CH(CH$_3$)$_2$, —CH(CH$_3$)C$_2$H$_5$, —CO$_2$H, or —CH$_2$—C$_6$H$_5$, (see Wheeler, W. J. et al. *J. Med. Chem.* 22: 657 (1979));

(c) Pivaloyloxymethyl (—CH$_2$—O—CO—C(CH$_3$)$_3$) (see Wheeler, W. J. et al, *J. Med. Chem.* 20: 1159 (1977));

(d) Phthalidyl:

(see Binderup, E. et al *J. Antibiot.* 24: 767 (1971));

(e) Probenecidoxylmethyl (see Christensen, B. G. et al, U.S. Pat. No. 3,931,150 (1976));

(f) Or a radical of the formula:

where p is an integer from 0 to 5,

R$^{14}$ is hydrogen, lower alkyl, aromatic such as or phenyl, pyridyl, or naphthyl,

R$^{15}$, R$^{16}$ and R$^{17}$ are the same or different and selected from the group consisting of hydrogen and lower alkyl, or R$^{16}$ and R$^{14}$ together may form a 5- or 6- membered heterocyclic group, such as, for example:

(see Van Daehne et al, U.S. Pat. No. 3,951,957 (1976)).

Carboxyl-protecting groups W include. p-nitrobenzyl, o-nitrobenzyl, t-butyl, lower alkyl (especially —CH$_3$, or —C$_2$H$_5$), pyridinium propyl, and the like.

Preferred compounds of the invention are those of Formula II:

In Formula II, n, W, Z$^1$ and R$^4$ are as defined above.

In Formula II, the amino acid or peptidyl residue can be in the L or D configuration, preferably L.

Among preferred compounds within Formula II are those wherein R$^4$ is Cl. Most preferred are those wherein R$^4$ is Cl, n is 2 and both beta-chloroalanyl residues are in the L configuration.

The compounds of the invention are made with cephalothin (see Formula 1 in FIG. 1), or R$^1$ analogs thereof as starting materials. For a synthesis of cephalothin see, for example Chauvette, R. R. et al, *J. Amer. Chem. Soc.* 84: 3401 (1962); French Pat. No. 1,384,197 (1965).

Figure 1:
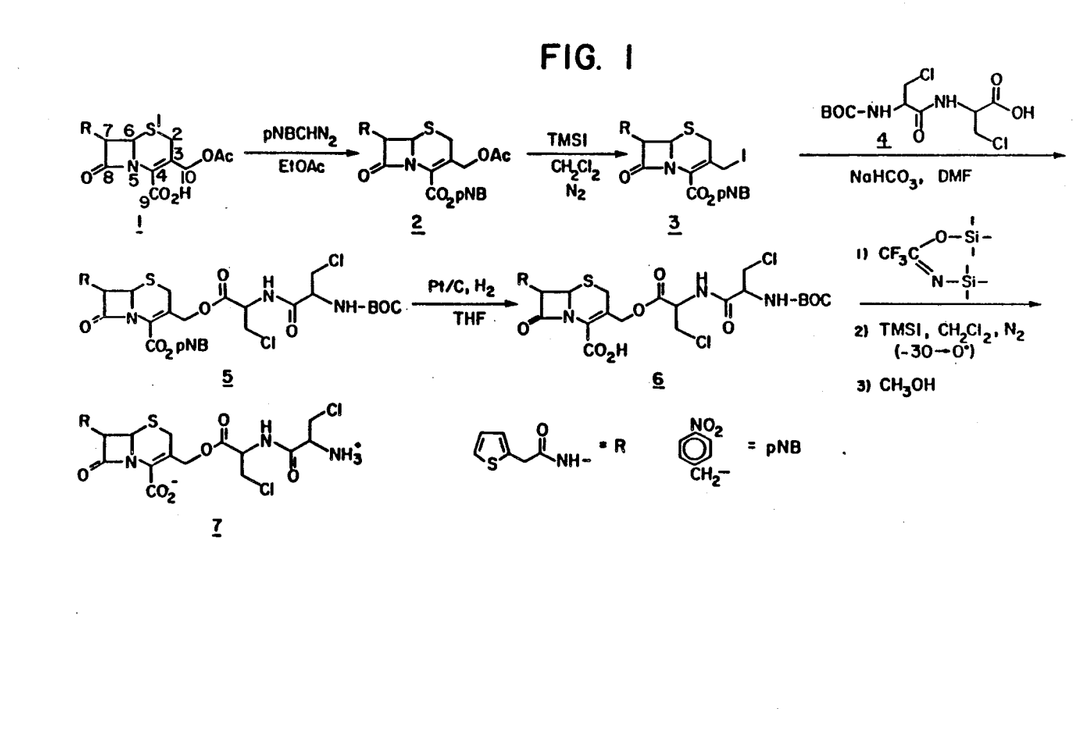
FIG. 1 shows the synthesis of 7-beta-(2-thienylacetamido)-3-(beta-chloro-L-alanyl-beta-chloro-L-alanyloxymethyl)-3-cephem-4-carboxylate (denoted as Compound 7).

For different R$^1$ substituents, compounds analogous to cephalothin can be utilized, by generating a cephalosphorin C$_{10}$-iodide (such as 3 in FIG. 1). This can be accomplished using cephalosporins with a variety of C$_{10}$-substituents, such as a thioether, a carbamoyl group (cefoxitin), or a thiotriazole or thiotetrazole (cefamandole). These groups are reactive with iodotrimethylsilane to afford the desired allylic iodide. See, e.g. Jung, M. E. et al *Tet. Lett.* 1977, 2659; Nudelman, A. et al *J. Org. Chem.* 43: 3788 (1978); Bonjouklian, R. et al, *Tet. Lett.* 1981, 3915; or Schmidt, A. H. *Aldrichimica Acta* 1981, 14, 31.

One synthetic scheme (as in FIG. 2) involves protection of the carboxylic acid group at C-9, such as for example with an ester, and reaction at C-10 to link appropriate amino acid or peptidyl residues. For example, a C-10 hydroxyl group can be oxidized to an aldehyde, followed by reaction with tosyl hydrazine, butyllithium and thermal decomposition to yield a diazoalkyl derivative. This derivative can then be reacted with an N-protected amino acid or peptidyl residue, generating a C-10 amino acid or peptidyl ester linked through a terminal carboxyl group. Deprotection of the corresponding amino terminal group and of the carboxylic acid group at C-9 yields the desired final product.

Alternatively (as in FIG. 1), the C-10 acetyl derivative of a cephalosporin intermediate carrying a protected carboxylic acid group at C-9 can be reacted with trimethylsilyl iodide, to generate an intermediate iodide which can then be converted into the amino acyl or peptidyl ester by reaction with an in situ generated or preformed salt of an unsubstituted or substituted amino acid or peptide residue. Deprotection of the acid at C-9 and of the amino group of the amino acid or peptidyl group can then be achieved to generate free salts of the desired compounds.

Carbamate (—O—C(=O)—NH—)-linked amino acid derivatives can be made by reacting the $C_{10}$-hydroxyl cephem with phosgene (in the presence of propylene oxide or a mild base (e.g., $Et_3N$, pyridine) to scavenge the HCl generated); this affords a cephem $C_{10}$-chloroformate (III) (R' is normally a protecting group such as p-nitrobenzyl, or may be W, supra).

The chloroformate III is, in turn, reacted with an appropriately carboxyl-protected amino acid or peptidyl derivative ($H_2N$—R'') to give a cephem $C_{10}$-carbamate, such as IV. Deprotection of the $C_9$-and amino acid or peptidyl carboxylate follows.

Amino acid ethers at C-10 can be made by the following method. An appropriately alpha-carboxyl- and alpha-amino-protected serinyl residue or a similarly C- and N-terminal protected serinyl-containing peptidyl unit are reacted with base (e.g., n-butyllithium) to give the salt of the serine beta-hydroxyl group (that is, R—OH to R—OH to R—$O^-M^+$) which, in turn, is reacted with a cephem iodide (such as e.g., compound 3) or cephem diazo compound (such as e.g., compound 13). Either reaction will afford the desired $C_{10}$-serinyl ether. The route involving a diazo cephem can be facilitated by rhodium (II) acetate catalysis (see, Melliels, D. G. et al., *Tet. Lett.* 21: 2786 (1980); Saltzmann, T. N. et al., *Tet. Lett.* 21: 1193 (1980); Ratcliffe, R. W. et al., *Tet. Lett.* 21: 31 (1980); Saltzmann, T. N. et al., *J. Amer. Chem. Soc.* 102: 6161 (1980); Paulissen, R. et al., *Tet. Lett.* 24: 2233 (1983)). Deprotection of the carboxyl and amino groups follows.

Thioethers, using cysteines and cysteinyl peptides can be obtained by similar synthetic manipulation.

The preparation of halogenated amino acids or peptides can be found, for example, in Kam-Sing Cheung et al; *J. Med. Chem.* 26:1733 (1983)) or in Mobashery, S. Ph.D. Thesis, University of Chicago, 1985, both herein incorporated by reference. The former reference also shows the preparation of propargylglycyl dipeptides.

Amino acids or peptidyl residues of either L or D configuration are readily available commercially or synthetically. Beta-cyanoalanine, and the O-carbamoyl derivative of seine are also available commercially.

The cephalosporin compounds of the invention are useful for treating a wide range of bacteria, both of the Gram-positive and Gram-negative species. Of particular interest are strains that display widespread resistance to conventional beta-lactam antibiotics. The compounds of the invention are therefore useful in the treatment of bacterial infections in individuals carrying the same.

Compounds wherein n (as defined above) is greater than 1, such as those including dipeptidyl or higher residues, are particularly useful for Gram-positive bacteria.

The compounds of the invention can be formulated in various pharmaceutical preparations adapted for administration in manners similar to those used for other cephalosporin compounds. Thus, one aspect of the invention involves pharmaceutical compositions for human beings or animals provided by using a conventional pharmaceutical carrier, diluent, and/or excipient with an antibacterial amount of a desired compound.

In particular, emulsions, solutions, or suspensions in aqueous or oil-based vehicles can be formulated for injection. Suppositories can also be provided by using conventional suppository bases such as coconut oils or other glycerides.

The content of the active compounds in the composition varies depending on the administration route, but is usually above 0.1%, such as 5–99%, preferably 10–60%.

The amount of administration for human beings for most cephalosphorins is usually in the range from about 1 to 50 g preferably 5 to 15 g per day for an adult depending on the cephalosporin compound used, the body weight, age, and symptoms of the patient, the nature of the infection and route or frequency of administration.

Having now generally described this invention, the same will become better understood by reference to certain examples which are included herein for purposes of illustration only and are not intended to be limiting unless otherwise specified.

MATERIALS AND METHODS

Ultraviolet and visible spectrophotometric analyses were carried out using a Perkin Elmer 559-Spectrophotometer. Proton NMR spectra were obtained at 500 MHz using a DS-1000 instrument, equipped with a Nicolet 1180 computer, with tetramethylsilane, in $CDCl_3$ in DMSO-$d_6$, or sodium 3-(trimethylsilyl)propionate, in $D_2O$, as the internal references. Chemical shift values ($\delta$) are given in ppm. Infrared spectra were obtained using a Perkin Elmer 283 Spectrometer. Melting points were taken on a Hoover Uni-Melt apparatus, and are uncorrected. Fast atom bombardment (FAB) mass spectral data were obtained using a VG7070 Spectrometer.

*Escherichi coli* TEM beta-lactamase was purchased from Applied Microbiology and Research, Porton Down, U.K. L-Alanyl-L-alanine was purchase from Sigma; N-BOC-LAla-LAla and N-BOC-beta-Cl-LAla-beta-Cl-LAla were prepared as described previously. Cheung et al supra. All other reagents were of the best grade commercially available.

CHEMICAL PREPARATIONS

Example 1

Preparation of
7-beta-(2-thienylacetamido)-3-(beta-chloro-L-alanyltachloro-L-alanyl-beta-chloro-L-alanyloxymethyl)-3-cephem-4-carboxylate The title cephem (7 in FIG. 1) was chosen as the first synthetic target. The key preparative reaction was coupling of the allylic iodide 3 with the dipeptide 4, which proceeded readily under mild conditions (62%, 3hrs.) Deprotection of 5 was the major challenge in the synthesis. For example, replacement of Pt with Pd or Rh in 5 to 6 gave, together with the desired removal of the $C_9$-nitrobenzyl group, the undesired reductive cleavage of the newly-formed C$_{10}$-ester. Similarly, methods routinely used for removal of the BOC-group from simple peptides, when applied to 6, gave cleavage of either the beta-lactam or the C$_{10}$-ester. However, platinum-catalyzed hydrogenolysis applied to 5, prior to removal of the BOC-group, gave 6 as the single product. The conversion 6 to 1 involved: (1) silylation of the C$_9$-carboxylate of 6; (2) treatment with TMSI to effect substitution of the N-BOC group with a silyl carbamate; and (3) methanolysis.

Compound 2. Yield, 84% overall from cephalothin; the crystals sintered at 99° C. and melted at 147°–148° C.; IR (CHCl$_3$): 1791, 1739, 1734, 1683, 1349 cm$^{-1}$; R$_f$ 0.41 (3:1, benzene/ethyl acetate); $^1$H NMR (CDCl$_3$): δ2.06 (s, 3H, methyl), 3.37, 3.54 (2d, 2H, C-2, J=18.5 Hz), 3.85 (s, 2H, side-chain methylene), 4.79, 5.12 (2d, 2H, C-10, J=13.5 Hz), 4.96 (d, 1H, C-6, J=4.9 Hz), 5.30, 5.35 (2d, 2H, benzylic, J=13.0 Hz), 5.86 (m, 1H, C-7), 6.20 (d, 1H, NH, J=9.1 Hz), 6.97 (m, 2H, thienyl), 7.25 (m, 1H, thienyl), 7.55, 8.20 (2d, 4H, phenyl, J=8.6 Hz); anal. (C$_{23}$H$_{21}$N$_3$O$_8$S$_2$) C, H, and N.

Compound 3. Yield, 82%; mp 142°–145° C. (dec.); IR (CHCl$_3$): 1792, 1652, 1336, 1112 cm$^{-1}$; R$_f$ 0.52 (3:1, benzene/ethyl acetate); $^1$H NMR (CDCl$_3$) 6 3.48, 3.76 (2d, 2H, C-2, J=18.1 Hz), 3.85 (s, 2H, sidechain methylene), 4.37 (s, 2H, C-10), 3.96 (d, 1H, C-6, J=5.0 Hz), 5.29, 5.37 (2d, 2H, benzylic, J=13.1 Hz), 5.80 (m, 1H, C-7), 6.22 (d, 1H, NH-side chain, J=9.0 Hz), 7.00 m, 2H, thienyl), 7.26 (m, 1H, thienyl), 7.56, 8.20 (2d, 4H, phenyl, J=8.6 Hz); anal. (C$_{21}$H$_{18}$N$_3$O$_6$S$_2$I) C, H, N and I.

Compound 5 p-Nitrobenzyl 7-beta-(2-thienylacetamido)-3-[N-t-butoxycarbonyl)-beta-chloro-L-alanylbeta-chloro-L-alanyloxymethyl]-3-cephem-4-carboxylate.

The iodide 3 (2.0 g, 3.34 mmol), N-t-butoxycarbonyl beta-Cl-LAla-beta-Cl-LALA (4, 1.14 g, 4.34 mmol), and NaHCO$_3$ (420 mg, 50 mmol) were stirred in 40 mL DMF for 3 hrs at room temperature. The solution was diluted with 100 mL ethyl acetate and washed with saturated CaCl$_2$ (3×), water, saturated NaHCO$_3$, and water. The ethyl acetate layer was dried over MgSO$_4$ and evaporated to dryness. The residue was a mixture of 20% Δ$^2$- and 80% Δ$^3$-isomers (determined by $^1$H NMR); R$_f$ 0.25 and 0.34 respectively (1:1, benzene/ethyl acetate). The isomers cold be purified on silica gel or committed to the following oxido-reductive sequence.

The residue was dissolved in 15 mL CHCl$_3$ and was reacted with a solution of 85% m-chloroperoxybenzoic acid (680 mg, 3.94 mmol) in 20 mL CHCl$_3$ at room temperature. Within 10 min some product had precipitated out of the solution. More CHCl$_3$ (50 mL) was added and the solution was stirred for 50 min more. The solution was diluted up to 200 mL to dissolve all of the precipitate and the solution was washed with saturated NAHCO$_3$ (2×), water, dried over MgSO$_4$ and evaporated to dryness.

The residue and stannous chloride dihydrate (1.9 g, 8.4 mmol) were dissolved in 50 mL DMF and chilled in an ice-bath. Acetyl chloride (10.0 mL, 140 mmol) was added and the solution was stirred for 45 min at room temperature. The solution was diluted with 100 mL ethyl acetate and it was washed with saturated CaCl$_2$ (3×), and water (2×). The organic layer was dried over MgSO$_4$ and evaporated in vacuo. Subsequent crystallization from CH$_2$Cl$_2$/isopropyl ether afforded 1.74 g of a crystalline product.

Yield, 62%; mp 133.5°–135° C.; IR (CHCl$_3$ film): 1790, 1735, 1725, 1690, 1668 cm$^{-1}$; Rf 0.23 (1:3, ethyl acetate/benzene); $^1$H NMR (CDCl$_3$): δ1.48 (s, 9H, t-butyl), 3.35 (d, 1H, C-2, J=18.6 Hz), 3.58 (d, 1H, C-2, J=18.8 Hz), 3.72 (dd, 1H, beta$_2$ HA, J=4.9 and 11.2 Hz). 3.87 (dd, beta$_1$-HA, J=3.4 and 11.5 Hz), 3.84 (s, 2H, side chain methylene), 3.87 (dd, beta$_1$-H$_B$, J=3.2 and 11.5 Hz), 4.02 (dd, beta$_2$- H$_B$, J=4.1 and 11.2 Hz), 4.51 (br s, 1H, a$_2$-methine), 4.87, 5.31 (2d, 2H, C-10, J=13.6 Hz), 4.94 (m, 1H, a$_1$-methine 4.97 (d, 1H, C-6, J=4.8 Hz), 5.20 (br s, 1H, N$_2$-H), 5.30, 5.36 (2d, 2H, benzylic, J=13.0 Hz), 5.85 (m, 1H, C-7), 6.22 (d, 1H, NH-side chain, J=8.9 Hz), 6.98 (m, 2H, thienyl), 7.11 (d, 1H, N$_1$-H, J=7.5 Hz), 7.25 (m, 2H, thienyl), 7.55 (d, 2H, phenyl, J=8.6 Hz), 8.20 (d, a$_2$-H, phenyl, J=8.6 Hz); anal. (C$_{32}$H$_{36}$N$_5$O$_{11}$S$_2$Cl$_2$) C, H, and N. (Each of the two prochiral beta-methylene hydrogens of beta-chloroalanine derivatives resolves into a doublet of doublets (ABX system, X=alpha-H) in the 500 MHz spectrum. The upfield signal was arbitrarily assigned HA and the downfield resonance H$_B$.)

Compound 7: 7-beta-(2-thienylacetamido)-3-(beta-chloro-L-alanyl-beta-chloro-L-alanoloxymethyl)-3-cephem-4-carboxylic acid.

The cephem ester 5 (800 mg, 1.0 mmol) was dissolved in 40 mL THF, and this solution was transferred to a pre-equilibrated suspension of 10% Pt/C (800 mg) under H$_2$. The solution was reacted for 4 hrs with three H$_2$ changes during the course of the reaction. The catalyst was filtered and the filtrate was concentrated to 15 mL in vacuo. The solution was reacted with a solution of NaHCO$_3$ (126 mg, 1.5 mmoles) in 10 mL water for 20 min. The remaining THF was evaporated. The aqueous layer was washed with ethyl acetate (3×) and, subsequently, twice filtered through celite. The aqueous layer was acidified to pH 1.5 with 1N HCl, and ethyl acetate extractions (3×) were made. The combined organic layers were washed with water, dried over MgSO$_4$, and evaporated to dryness to yield 325 mg (49%) of the free acid 6.

A solution of 6 in 5 mL dry CH$_2$Cl$_2$ was reacted with bis-(trimethylsilyl)trifluoroacetamide (2.6 mL, 9.8 mmol) under N$_2$. This solution was stirred for 45 min at room temperature and then evaporated to dryness under high vacuum. The residue was dissolved in 10 mL dry CH$_2$Cl$_2$ and chilled to −30° C. Iodotrimethylsilane (41.6 uL, 0.29 mmol) was then added dropwise over 1–2 min under N$_2$ The solution was allowed to warm to 0° C. and was stirred for an additional 10 min at 0° C. Methanol (400 uL, 9.8 mmoles) was added and the stirring was continued at the same temperature for 5 min. The solution was then warmed to room temperature, and the stirring was continued for 10 min. Ether was added to precipitate the product. The precipitate was washed with chloroform and acetone followed by drying under vacuum to give 125 mg of the product. Yield, 75% (from the free acid); mp 136°–137° C.; IR(-nujol): 3250, 1774, 1717, 1689, 1654, 1372 cm$^{-1}$; R$_f$0.61 (4:1:1, n-butanol/H$_2$O/CH$_3$CO$_2$H); $^1$H NMR (DMSO-d$_6$): 3.42, 3.60 (2d, 2H, C-2, J=18.0 Hz), 3.47, 3.79 (2d, 2H, side chain methylene, J=15.4 Hz), 3.83 (dd, beta$_1$-H$_4$, J=6.2 and 11.3 Hz), 3.87 (dd, beta$_1$ H$_B$, J=4.3 and 11.3 Hz), 3.89 (dd, beta$_2$-H$_4$, J=5.0 and 11.2 Hz), 3.96 (dd, beta$_2$-H$_B$, J=4.5 and 11.2 Hz), 4.73 (m, 1H, alpha$_2$-methine), 4.81, 5.12 (2d, 2H, C-10, J=12.5 Hz), 5.02 (d, 1H, C-6, J=5.1 Hz), 5.66 (m, 1H, C-7), 6.92 (m, 2H, thienyl), 7.43 (m, 1H, thienyl), 9.03 (d, 1H, NH-side chain, J=8.2 Hz); anal. (C$_{22}$H$_{23}$N$_4$S$_2$O$_9$Cl$_2$F$_3$) C, H, and N; MS (FAB+), m/z 567 (M+1). (The zwitterionic product precipitates as an amorphorus solid, trapping acetone, which gave unreliable data for elemental analysis. Thus, the trifluoroacetate salt of 7 was prepared, for which good analytical data were obtained, by dissolving the zwitterionic 7 (10 mg) in 0.5 mL of freshly-distilled trifluoroacetic acid. The solution was then rapidly (within 30 sec) evaporated under high vacuum; the residue was dissolved in 40 mL of water; and the salt was obtained by lyophilization.)

EXAMPLE 2

Figure 2:
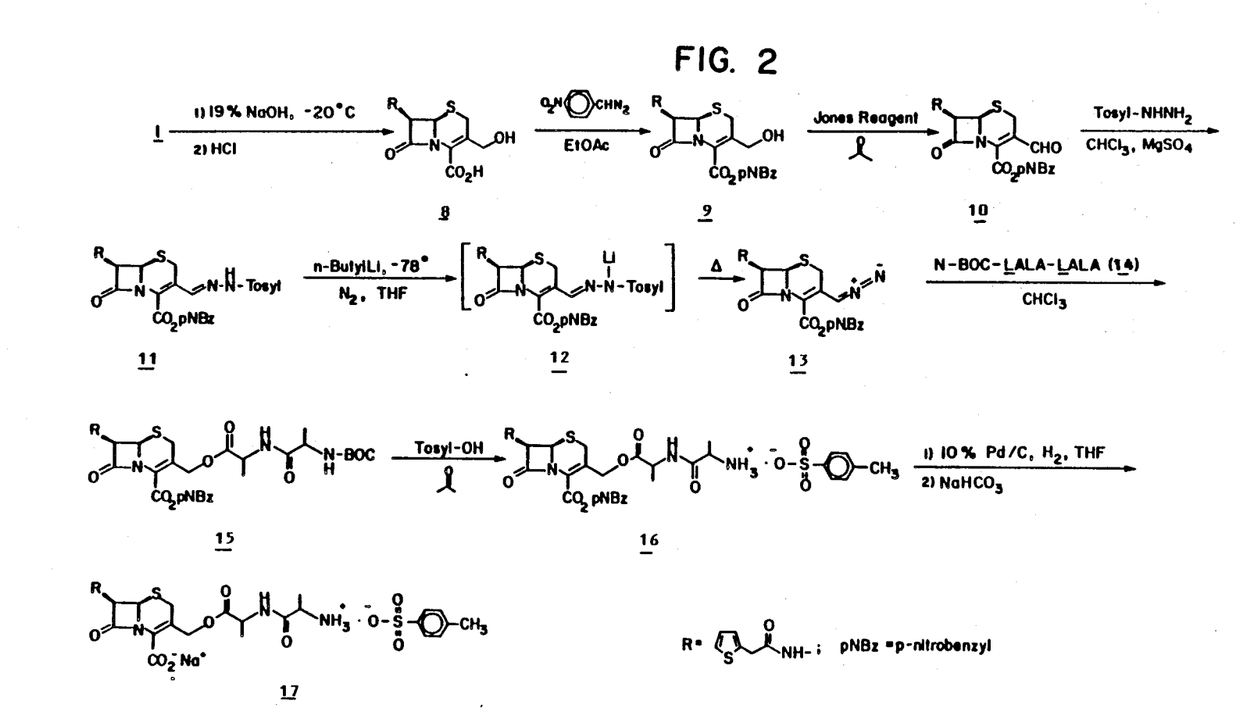
FIG. 2 shows the synthesis of 7-beta-(2-thienylacetamido)-3-(L-alanyl-L-alanyloxymethyl)-3-cephem-4-carboxylate (denoted as Compound 17 and shown as the p-toluenesulfonate, sodium salt). The starting material in this Figure is Compound 1, which is shown in FIG. 1.

Synthesis of Sodium 7-beta-(2-thienylacetamido)-3-(L-alanyl-L-alanyloxymethyl)-3-cephem-4-carboxylate, toluenesulfonic acid salt, (FIG. 2, Compound 17)

Sodium cephalothin was obtained from the University of Chicago Hospitals and Clinics. The pharmaceutical preparation was homogeneous, as evidenced by its elution behavior on thin layer chromatograms, its IR spectrum and its 500 MHz $^1$H NMR spectrum.

The synthetic route for preparation of 17 is shown in FIG. 2. Cephalothin was readily deacylated by basic hydrolysis 1 to 8). This method occasionally gives also lactam ring-opened products (<5%) and a (1 to 8) $C_9,C_{10}$-lactone (<3%). In fact, the yield of the desired product was clearly dependent on the rapidity with which manipulations were made and on the scrupulous adherence to the reaction conditions (especially temperatures) given below. The yields and purity of the product generally improve as one becomes more facile in carrying out the operations. Nonetheless, the lactone and the lactam-hydrolyzed cephem impurities are easily removed by fractional crystallization, or by silica gel chromatography, following esterification of the $C_9$-carboxylic acid.

The key step of FIG. 2 is coupling of the cephem diazide (13) to the N-BOC-dipeptide (14), a reaction which proceeds rapidly and cleanly at ambient temperature. The diazide 13 is a versatile reagent for the preparation of a number of $C_{10}$-esters of cephems.

Preparation of p-nitrophenyldiazomethane p-Nitrobenzaldehyde (25 g, 0.165 mol) and p-toluenesulfonhydrazide (37 g, 0.198 mol) were refluxed for 30 min in 900 mL of ethyl acetate in the presence of 40 g of anhydrous $MgSO_4$. The mixture was then filtered, washed twice with 0.5N HCl, once with water and then dried over $MgSO_4$. Evaporation gave 52.5 g (100%) p-nitrobenzyltosylhydrazone as yellow crystals. Silica gel TLC gave $R_f$=0.63 (benzene/ethyl acetate, 3:1); mp 143°-146° C.

Nitrophenyldiazomethane was prepared according to the procedure of Engels and Schlaeger (*J. Med. Chem.*, 20:907-911 (1977)). p-Nitrobenzyltosylhydrazone (25 g, 78 mmol) was dissolved in a mixture of 2N KOH (117.5 mL) and water (1.5 L), and the solution was warmed in an oil bath at 50°-55° C. for 3 hrs. The resulting suspension was then cooled to room temperature and filtered. The filtered yellow crystals were washed with water until the filtrate reached a pH of 6.1-6.3, and then they were dried in vacuo. The product yield of p-nitrophenyldiazomethane was 70% (8.9 g); mp 78°-79° C. (lit., 80° C.); IR (mineral oil) 2069 cm$^{-1}$ (lit., 2064 cm$^{-1}$).

Compound 8: 7 Beta-(2-thienylacetamido)-3-hydroxymethyl-3-cephem-4-carboxylic acid To a 20 mL aqueous solution of sodium cephalothin (1; 4.0 g, 9.97 mmol) at 0° C. was added, in one portion, 40 mL of NaOH (19%), which had been cooled previously to −20° C. The reaction mixture was stirred at −10° C. for 135 seconds and then quenched by the rapid addition of glacial acetic acid (13 mL, at room temperature). The reaction was then transferred to an ice-water bath, and the pH of the mixture was immediately lowered to 1.5 by the addition of concentrated HCl, which previously had been cooled to a slush. The resulting white solid was filtered, washed twice with cold water and dried in vacuo. Yield, 3.0 g, 87%; sintered 135°-190° C., melted 214°-215° C. (dec.); IR (Nujol); 3400, 1760, 1717, 1648 cm$^{-1}$; $R_f$ 0.66 (4:1:1, n-butanol/H$_2$O/CH$_3$CO$_2$H); $^1$H NMR (D$_2$O/NaHCO$_3$): δ3.41, 3.61 (2d, 2H, C-2, J=17.8 Hz), 3.86, 3.92 (2d, 2H, side chain methylene, J=15.8 Hz), 4.21, 4.27 (2d, 2H, C-10, J=12.9 Hz), 5.08 (d, 1H, C-6, J=4.6 Hz), 5.59 (d, 1H, C-7, J=4.6 Hz), 7.03 (m, 8, 2H, thienyl), 7.35 (m, 1H, thienyl).

Compound 10: p-Nitrobenzyl 7-beta-(2-thienylacetamido)-3-formyl-3-cephem-4-carboxylate Deacetylcephalothin (8; 8.5 g, 24.0 mmol) was reacted with p-nitrophenyldiazomethane (4.3 g, 26.4 mmol) in 360 mL of ethyl acetate for 1 hr at 60°±3° C.; the mixture was then refluxed for 20 min. The reaction mixture was hot filtered, and the filtrate was washed once with saturated NaHCO$_3$, twice with water and then dried over MgSO$_4$. The ethyl acetate was stripped, and 6.2 g (53%) of 9 was obtained by slow crystallization from methylene chloride/isopropyl ether.

The orange, crystalline solid was dissolved in acetone (210 mL), and Jones reagent (2.0 mL of a 2.5M solution) was added dropwise. After 12 min, isopropyl alcohol (7.9 mL) was added, and the mixture was evaporated in vacuo to 30 mL. Water (150 mL) was added, and the organic phase was extracted into ethyl acetate (3×2200 mL). The combined ethyl acetate fractions were washed with, in turn, water, saturated NaHCO$_3$, water, 1N HCl and water. The resulting emulsion was dispersed by warming during a final water wash. The ethyl acetate fraction was recovered, dried over MgSO$_4$ and evaporated in vacuo; the residue was precipitated from CH$_2$Cl$_2$/hexane, giving 4.2 g of a dirty yellow solid.

This crude product was then subjected to silica gel (60-200 mesh) column chromatography (3.8×20 cm), in 1.4 g increments, using 20% ethyl acetate in benzene as the eluting solvent. Fractions containing the band of yellow chromophore were pooled and evaporated to dryness. Crystallization of the residue from CH$_2$Cl$_2$/hexane afforded 2.0 g of 10 as bright yellow crystals. Yield, 24% overall from 8; mp 143°-145° C. (dec); IR (CHCl$_3$ film): 1799, 1734, 1669 cm; $R_f$ 0.53 (1:3, ethyl acetate/benzene); $^1$H NMR (CDCl$_3$): δ3.29, 4.02, (2d, 2H, C-2, J=18.5 Hz), 3.87 (s, 2H, side chain methylene), 5.03 (d, 1H, C-6, J=4.9 Hz), 5.42 (s, 2H, benzylic), 5.96 (m, 1H, C-7), 6.24 (d, 1H, NH, J=8.9 Hz), 7.00 (m, 2H, thienyl), 7.27 (m, 1H, thienyl), 7.56 (d, 2H, phenyl, J=8.5 Hz), 8.22 (d, 2H, phenyl, J=8.5 Hz), 9.83 (s, 1H, formyl); anal. (C$_{21}$H$_{17}$N$_3$S$_2$O$_7$) C, H, and N.

Compound 11: p-Nitrobenzyl7-beta-(2-thienylacetamido)-3-(p-toluenesulfonhydrazonoformyl)-3-cephem-4-carboxylate The aldehyde 10 (2.0 g, 4.10 mmol), p-toluenesulfonhydrazide (0.99 g, 5.32 mmol) and dry MgSO$_4$ (7.2 g) were stirred in 320 mL of chloroform for 22 hrs at room temperature. The mixture was then filtered, washed twice with both 0.5N HCl and water, dried over MgSO$_4$ and filtered. The filtrate was evaported in vacuo to give 2.7 g of 11 as shiny, yellow crystals. Yield, 100%; mp 77°-79° C.; IR (CHCl$_3$ film); 1788, 1727, 1678 cm$^{-1}$; R$_f$ 0.37 (1:3, ethyl acetate/benzene); $^1$H NMR (CDCl$_3$): δ2.42 (s, 3H, methyl), 3.36, 4.01 (2d, 2H, C-2, J=18.6 Hz), 3.84 (s, 2H, side chain methylene), 4.96 (d, 1H, C-6, J=5.1 Hz), 5.25, 5.29 (2d, 2H, benzylic [ester], J=13.0 Hz), 5.87 (m, 1H, C-7), 6.45 (d, 1H, NH-side chain, J=9.2 Hz), 6.97 (m, 2H, thienyl), 7.23 (m, 1H, thienyl), 7.28 (d, 2H, phenyl [tosyl], J=8.1 Hz), 7.48 (d, 2H, phenyl [ester], J=8.7 Hz), 7.76 (d, 2H, phenyl [tosyl], J=8.1 Hz), 8.11 (s, 1H, NH-tosyl), 8.13 (d, 2H, phenyl [ester], J=8.7 Hz); anal. (C$_{28}$H$_{25}$N$_5$S$_3$O$_8$) C, H, and N.

Compound 13: p-Nitrobenzyl 7-beta-(2-thienylacetamido)-3-diazomethyl-3-cephem-4-carboxylate The conversion 11 to 13 of FIG. 2 was carried out by modification of the methods of Fahey et al., *J. Med. Chem.* 20:907-911 (1977). A solution of the tosylhydrazone 11 (1.0 g, 1.53 mmol) in dry THF (20 mL) was reacted with n-butyllithium (1.13 mL of a 1.28M solution in n-hexane, 1.45 mmol) under N$_2$ at −78° C. The solution was brought to room temperature until it turned clear and was then briefly warmed to 40° C. The mixture was filtered and evaporated to a small volume (5-7 mL) and loaded onto a silica gel column (60-200 mesh, 3.8×10 cm), packed in ethyl acetate. The column was flashed with ethyl acetate/chloroform (1:1). The colored fractions were combined and evaporated to dryness, which afforded 670 mg of 13 as amber crystals. Yield, 88%; mp 54°-55° C.; IR (CHCl$_3$ film): 2072, 1775, 1738, 1650 cm$^{-1}$; R$_f$ 0.75 (1:1 ethyl acetate/CHCl$_3$); $^1$H NMR (CDCl$_3$): δ3.12, 3.25 (2d, 2H, C-2, J=15.9 Hz), 3.87 (s, 2H, side chain methylene), 5.04 (d, 1H, C-6, J=4.1 Hz), 5.17, 5.37 (2d, 2H, benzylic, J=13.5 Hz), 5.54 (m, 1H, C-7), 6.53 (d, 1H, NH, J=7.8 Hz), 6.75 (s, 1H, C-10), 6.98 (m, 2H, thienyl), 7.24 (m, 1H, thienyl), 7.54 (d, 2H, phenyl, J=8.4 Hz), 8.19 (d, 2H, phenyl, J=8.4 Hz).

Compound 15: p-Nitrobenzyl 7-beta-(2-thienylacetamido)-3-[(N-tert-butoxycarbonyl)-L-alanyl-L-alanyloxymethyl]-3-cephem-4-carboxylate.

The diazocephem (13; 0.67 g, 1.74 mmol) and N-BOC-LAla-LAla (14; 1.36 g, 5.22 mmol, 3 equiv.) were disolved in 2 mL chloroform for 5 min at room temperature; additional chloroform was added (18 mL), and the reaction was continued for 10 min. The solution was then washed twice with saturated NaHCO$_3$ and water, and the aqueous phase was retained. (Unreacted 14 may be recovered from the aqueous fractions by acidification (KHSO$_4$) to pH 1.5 and extraction of the free acid to ethyl acetate (3×). The combined ethyl acetate fracetions are washed with water, dried over MgSO$_4$ and evaporated in vacuo. N-BOC-LAla-LAla is then crystallized from ethyl acetate/hexane at −20° C.) The organic layer was dried over MgSO$_4$, evaporated to approximately 3 mL and spotted onto preparative thin layer plates (20×20 cm, 1500 u, silica gel); the plates were developed using 20% ethyl acetate/benzene. The UV-absorbing band at R$_f$ 0.20-0.38 was extracted from the silica gel, and crystallization from methylene chloride/hexane gave 464 mg of 15. Yield, 47%; mp 110°-112° C.; IR (CHCl$_3$ film); 1781, 1731, 1724, 1682 cm$^{-1}$; R$_f$ 0.34 (1:1, ethyl acetate/benzene); $^1$H NMR (CDCl$_3$): δ6 1.34 (d, 3H, beta$_2$-methyl, J=7.0 Hz), 1.39 (d, 3H, beta$_1$-methyl J=7.2 Hz), 1.45 (s, 9H, tert-butyl), 3.35, 3.54, (2d, 2H, C-2, J=18.6 Hz), 3.85 (s, 2H, side chain methylene), 4.15 (br s, 1H, alpha$_2$-methine), 4.51 (m, 1H, alpha$_1$-methine), 4.87, 5.21 (2d, 2H, C-10, J=13.6 Hz), 4.91 (d, 1H, N$_1$-H, J=7.2 Hz), 4.97 (d, 1H, C-6, J=4.9 Hz), 5.30, 5.35 (2d, 2H, benzylic, J=13.0 Hz), 5.86 (m, 1H, C-7), 6.60 (br s, 1H, N$_2$-H), 6.34 (d, 1H, NH-side chain, J=8.9 Hz), 6.97 (m, 2H, thienyl), 7.26 (m, 1H, thienyl), 7.55 (d, 2H, phenyl, J=8.6 Hz), 8.20 (d, 2H, phenyl, J=8.6 Hz); anal. (C$_{32}$H$_{37}$N$_5$O$_{11}$S$_2$) C, H, and N.

Compound 16: p-Nitrobenzyl 7-beta-(2-thienylacetamido)-3-(L-alanyl-L-alanylymethyl)-3-cephem-4-carboxylate, toluenesulfonic acid salt The [N-BOC-peptidyl] cephem ester 15, (150 mg, 0.20 mmol) and p-toluenesulfonic acid, monohydrate (81.8 mg, 0.42 mmol), were stirred in 0.5 mL acetone at room temperature for 4 hrs. A few mL of benzene were added and the resulting beige precipitate (100 mg) was filtered, washed with cold acetone and dried in vacuo. The filtrate was evaporated in vacuo. (The residue was dissolved in ethyl acetate (20 mL), washed three times with water, dried over MgSO$_4$ and evaporated to dryness. Recrystallization of the resulting residue from methylene chloride/hexane afforded unreacted 15, which could be reprocessed.) Yield, 61%; mp 158°-162° C., the compound changes color above 100° C.; IR (Nujol): 1770, 1740, 1669 cm$^{-1}$; R$_f$ 0.66 (4:1:1, n-butanol/H$_2$O/CH$_3$CO$_2$H); $^1$H NMR (DMSO-d$_6$): δ1.32 (d, 3H, beta$_2$-methyl, J=7.1 Hz), 1.35 (d, 3H, beta$_1$-methyl, J=7.2 Hz), 2.28 (s, 3H, methyl [tosyl]), 3.53, 3.62 (2d, 2H, C-2, J=16.3 Hz), 3.76 (s, 2H, side chain methylene), 3.90 (br s, 1H, alpha$_1$-methine), 4.37 (m, 1H, alpha$_2$-methine), 3.81, 5.05 (2d, 2H, C-10, J=13.2 Hz), 5.14 (d, 1H, C-6, J=4.8 Hz), 5.38, 5.45 (2d, 2H, benzylic, J=14.8 Hz), 5.76 (m, 1H, C-7), 6.94 (m, 2H, thienyl), 7.08 (d, 2H, phenyl [tosyl], J=7.6 Hz), 7.20 (m, 1H, thienyl), 7.46 (d, 2H, phenyl [tosyl], J=7.6 Hz), 7.68 (d, 2H, phenyl [ester] J=8.9 Hz), 8.03 (br m, 3H, free amine and N$_1$-H), 8.22 (d, 2H, phenyl [ester], J=8.9 Hz), 8.74 (br m, 1H, N$_2$-H), 9.10 (d, 1H, NH-side chain, J=7.6 Hz); anal. (C$_{34}$H$_{37}$N$_5$S$_3$O$_{12}$) C, H, and N.

Compound 17: Sodium 7-beta-(2-thienylacetamido)-3-(L-alanyl-L-alanyloxymethyl)-3-cephem-4-carboxylate, toluenesulfonic acid salt.

The tosyl salt of the cephem ester, 16 (50 mg, 0.062 mmol) was dissolved in 60 mL of THF, and this was added to a THF (15 mL) suspension of 10% Pd/C (50 mg), which had been pre-equilibrated with H$_2$. The reaction mixture was stirred at room temperature under H$_2$ for 30 min. Sodium bicarbonate (7.8 mg, 0.093 mmol) in 2 mL of water was added to the suspension, and the reaction was continued for an additional 30 min. The mixture was then filtered through celite and evaporated in vacuo to approximately 2 mL. Water (10 mL) and ethyl acetate (20 mL) were added, and the layers were separated. The aqueous phase was filtered and lyophilized to yield 25 mg of 17 as a white, powdery solid. Yield, 59%; IR (Nujol): 1775, 1735, br 1650, 1598 cm$^{-1}$; R$_f$, 0.35 (4:1:1, n-butanol/H$_2$O/ CH$_3$CO$_2$H); $^1$H NMR (D$_2$O) δ1.47 (d, 3H, beta$_2$-methyl, J=7.3 Hz), 1.55 (d, 3H, beta$_1$-methyl, J=7.1 Hz), 2.42 (s, 3H, tosyl methyl), 3.35, 3.64 (2d, 2H, C-2, J=17.9 Hz), 3.91, 3.96 (2d, 2H, side chain methylene, J=15.7 Hz), 4.08 (q, 1H, alpha$_1$-methine, J=7.1 Hz), =15.7 Hz) 4.50 (q, 1H, alpha$_2$-methine, J=7.3 Hz), 4.79, 5.04 (2d, 2H, C-10, J=12.4 Hz), 5.13 (d, 1H, C-6, J=4.7 Hz), 5.65 (d, 1H, C-7, J=4.7 Hz), 7.07 (m, 2H, thienyl), 7.36 (m, 1H, thienyl), 7.38 (d, 2H, phenyl, J=8.2 Hz), 7.72 (d, 2H, phenyl, J=8.2 Hz); anal. (C$_{27}$H$_{31}$N$_4$O$_{10}$S$_3$Na) C, H, and N; MS (FAB−), m/z 495 (M−1).

EXAMPLE 3

Preparation of 7-beta-(2-thienylacetamido)-3-(L-alanyloxymethyl)-3-cephem-4-carboxylic acid This compound was prepared as shown in FIG. 2, but replacing compound 14 thereof with N-BOC-LAla. The synthetic manipulations were identical to those shown to prepare dipeptidyl 17.

Analytical data for title compound: Yield, 53%; mp 140°–140.5° C.; IR (KBr pellet): 3600–2700 (br), 1778, 1740, 1660, 1524, 1396 cm$^{-1}$; R$_f$ 0.55 (4:1:1, n-butanol/CH$_3$CO$_2$H/H$_2$O); $^1$H NMR (DMSO-d$_6$): δ1.43 (d, 3H, beta-methyl, J=7.2 Hz), 3.56, 3.68 (2d, 2H, C-2, J=18.1 Hz), 3.75, 3.79 (2d, 2H, side-chain methylene, J=15.2 Hz), 4.08 (m, 1H, alpha-methine), 4.87, 5.15 (2d, 2H, C-10, J=13.1 Hz), 5.07 (d. 1H, C-6, J=4.7 Hz), 5.69 (m, 1H, C-7), 6.92 (m, 2H, thienyl), 7.33 (m, 1H, thienyl), 9.07 (d, 1H, NH-side chain, J=8.1 Hz); anal. (C$_{19}$H$_{20}$N$_3$S$_2$O$_8$F$_3$) C, H, and N; MS(FAB+), m/z 426 (m+1).

EXAMPLE 4

Preparation of 7-beta-(2-thienylacetamido)-3(beta-chloro-L-alanyloxymethyl)-3-cephem-4-carboxylic acid This compound was prepared as shown in FIG. 1, but replacing compound 4 therein with N-BOC-beta-Cl-L Ala. The synthetic manipulations were identical to those shown to prepare dipeptidyl 7.

Analytical data for title compound: Yield: 50%; mp 114°–117° C.; IR (Nujol): 3280, 1773, 1738, 1682, 1375 cm$^{-1}$; R$_f$ 0.55 (4:1:1, n-butanol/CH$_3$CO$_2$H/H$_2$O); $^1$H NMR (DMSO-d$_6$): δ3.56, 3.68 (2d, 2H, C-2, J=18.0 Hz), 3.74, 3.79 (2d, 2H, side-chain methylene, J=15.2 Hz), 4.03 (dd, 1H, beta-H$_A$, J=3.3 and 12.4 Hz), 4.15 (dd, 1H, beta-H$_B$, J=3.9 and 12.4 Hz), 4.69 (m, 1H, alpha-methine), 4.96, 5.20 (2d, 2H, C-10, J=12.8 Hz), 5.06 (d, 1H, C-6, J=4.8 Hz), 5.68 (m, 1H, C-7), 6.93 (m, 2H, thienyl), 7.34 (m, 1H, thienyl), 9.08 (d, 1H, NH-side chain, J=8.1 Hz); anal. (C$_{19}$H$_{19}$N$_3$S$_2$O$_8$ClF$_3$) C, H, and N; MS(FAB+), m/z 461 (M+1).

BIOLOGICAL EXAMPLES

The antibacterial effects of compounds of the invention have been assessed by determination of the minimum inhibitory concentration (M.I.C.) value against a variety of Gram-negative and -positive bacteria. The microbial susceptibility data for four compounds, together with those for the antibacterial dipeptide beta-Cl-LAla-beta-Cl-LAla, are given in Table I.

TABLE I

Minimum Inhibitory Concentrations (uM)$^a$ for Synthetic Cephems and for the Dipeptide beta-chloro-L-Ala-beta-chloro-L-ala.

| Bacterial species | X$^3$ = —Ala (b) | X$^3$ = —Cl—Ala (c) | X$^3$ = —Ala—Ala (d) | X$^3$ = —Cl—Ala— —Cl—Ala (e) | X$^3$ = Dipeptide (f) |
|---|---|---|---|---|---|
| (GRAM-NEGATIVE:) | | | | | |
| Enterobacter cloacae | >200 | 100 | 200 | 12.5 | 12.5 |
| Enterobacter areogenes | >200 | >200 | >200 | 200 | 25 |
| Psuedomonas aeruginosa | >200 | >200 | >200 | >200 | >200 |
| Klebsiella pneumoniae | >200 | >200 | >200 | >200 | >200 |
| Serratia marcescens | >200 | >200 | >200 | >200 | >200 |
| Salmonella typhimurium | >200 | 100 | 100 | 50 | 200 |
| Salmonella typhimurium LT 2 | 50 | 25 | 25 | 25 | 200 |
| Shigella flexneri | 100 | 100 | 100 | 50 | 200 |
| Morganella morganii | 100 | 100 | 100 | 50 | 200 |
| Escherichia coli JSR-O | 100 | 100 | 200 | 12.5 | 12.5 |
| Escherichia coli JSR-O Cl-Pep$^{R(g)}$ | >200 | >200 | 100 | 50 | >200 |
| Escherichia coli DB4548 | 50 | 50 | 50 | 6.25 | 6.25 |
| Escherichia coli CR | 100 | 50 | 200 | 12.5 | 12.5 |
| Escherichia coli JSR-O pBR322$^{(h)(i)}$ | 50 | 100 | >200 | 6.25 | 12.5 |
| Escherichia coli Ceph$^{R(j)}$ | >200 | >200 | >200 | 12.5 | 3.12 |
| Hemophilus influenzae 236 | 50 | 25 | 50 | 25 | >200 |
| Hemophilus influenzae 487$^{(h)}$ | 50 | 25 | 12.5 | 3.12 | ≦0.78 |
| Hemophilus influenzae 238 | ≦0.78 | ≦0.78 | ≦0.78 | ≦0.78 | 12.5 |
| (GRAM POSITIVE:) | | | | | |
| Corynebacterium JKR-2285$^{(j)}$ | >200 | >200 | >200 | 3.12 | 0.78 |
| Corynebacterium JKM-4754$^{(j)}$ | >200 | >200 | >200 | 3.12 | 0.78 |
| Streptococcus faecalis | >100 | 200 | 50 | 12.5 | 6.25 |
| Streptococcus agalactiae | ≦0.78 | ≦0.78 | ≦0.78 | ≦0.78 | ≦0.78 |
| Staphylococcus aureus T-4624-8 Pen$^{R(h)}$ | 100 | 6.25 | 25 | ≦0.78 | 1.56 |
| Staphylococcus aureus H-2690-8$^{R(h)}$ | 100 | 6.25 | 25 | ≦0.78 | 1.56 |
| Staphylococcus aureus PSL-13 Pen$^{R(h)}$ | 200 | 25 | >200 | ≦0.78 | 1.56 |
| Staphylococcus aureus PSL-14 Pen$^{R(h)}$ | >200 | 25 | >200 | 1.56 | 12.5 |
| Staphylococcus aureus PSL-15 Pen$^{R(h)}$ | 100 | 12.5 | >200 | 1.56 | 12.5 |
| Staphylococcus aureus PSL-16 Pen$^{R(h)}$ | >200 | 255 | 200 | 1.56 | 12.5 |
| Staphylococcus epidermidis MO1554(P$^S$M$^S$)$^{(k)}$ | ≦0.78 | ≦0.78 | ≦0.78 | ≦0.78 | ≦0.78 |
| Staphylococcus epidermidis 1239(P$^R$M$^R$)$^{(k)}$ | ≦0.78 | ≦0.78 | ≦0.78 | ≦0.78 | ≦0.78 |

TABLE I-continued

Minimum Inhibitory Concentrations (uM)$^a$ for Synthetic Cephems and for the Dipeptide beta-chloro-L-Ala-beta-chloro-L-ala.

| | where | | | | |
|---|---|---|---|---|---|
| Bacterial species | $X^3 =$ —Ala (b) | $X^3 =$ —Cl—Ala (c) | $X^3 =$ —Ala—Ala (d) | $X^3 =$ —Cl—Ala— —Cl—Ala (e) | $X^3 =$ Dipeptide (f) |
| *Staphylococcus epidermidis* ($P^R M^R$)$^{(k)}$ | 1.56 | ≦0.78 | ≦0.78 | ≦0.78 | ≦0.78 |

$^{(a)}$MIC values are typically reported in ug/mL. The MICs are reported in uM to facilitate a meaningful comparison of the approximate MICs among the tested compounds; an appreciation of the MIC values in ug/mL can be obtained by multiplying each value (μM) by 0.55 μM.
$^{(b)}X^3$ is (L)-CO—CH(CH$_3$)—NH$_2$
$^{(c)}X^3$ is (L)-CO—CH(CH$_2$Cl)—NH$_2$
$^{(d)}X_3$ is (L,L)-CO—CH(CH$_3$)—NH—CO—CH(CH$_3$)—NH$_2$
$^{(e)}X^3$ is (L,L)-CO—CH(CH$_2$Cl)—NHCO—CH(CH$_2$Cl)—NH$_2$
$^{(f)}$Beta-chloro-L-Ala-beta-chloro-L-Ala.
$^{(g)}$This ia an *E. coli* JSR-O strain selected for resistance to the peptide (f).
$^{(h)}$Possesses a beta-lactamase.
$^{(i)}$Contains the plasmid gene encoding the TEM beta-lactamase.
$^{(j)}$Resistant to cephalothin (MIC >200 uM);
$^{(k)}$P and M refer to penicillin and methicillin, respectively.

Two general trends can be observed by examination of Table I. First, when susceptibility to a cephem is seen, the Gram-positive organisms are exquisitely sensitive to the tested compound, whereas the Gram-negative organisms show somewhat higher MiC values. Second, compound (e), the chloroalanyl dipeptidyl cephem, is by-and-large a more potent antimicrobial agent than the other three cephalosporins (b), (c) and (d). Several comparisons illustrate this point.

In nearly a third of the cases examined (including *E. cloacae*, all of the susceptible *E. coli* strains, Corynebacterium strains and *S. faecalis*), (e) is the only cephalosporin with detectable activity. There are a substantial number of instances (including *E. cloacae*, all of the susceptible *E. coli* strains, *H. influenzae* 487 and all of the *S. aureus* strains) where sensitivity was observed to both (c) and (e) and no activity was seen for the cognate alanyl and dialanyl cephems (b) and (d), respectively.

Note that in these several cases, the peptidyl cephem (e) is invariably more potent an antibiotic than is the amino acid ester (c). This pattern of activity appears to reflect the susceptibility difference of sensitive microorganisms to beta-haloamino acids and to peptides containing these residues: beta-Cl-LAla-beta-Cl-LAla, for example, is consistently and dramatically more potent an antibacterial agent than is beta-Cl-LAla alone (Cheung et al., supra, 1983). *P. aeruginosa, S. marcescens* and *K. pneumoniae* are inherently insensitive to the haloalanyl dipeptide (f), and are also resistant to (e). Conversely, *S. aureus* strains, Corynebacterium JK strains, *S. faecalis, H. influenzae* strain 487, *E. coli* JSR-O and *E. cloacae* are sensitive both to peptide (f) and to the cephem (e). Additionally, as noted above, these organisms are relatively more sensitive to (e) than to any of the other cephems tested.

A comparison of the data for *E. coli* strains JSR-O and JSR-O Cl-Pep$^R$ is of special interest. *E. coli* Cl-Pep$^R$ is an *E. coli* JSR-O mutant which was selected for resistance to the dipeptide (f). Whereas the parental strain is sensitive to (e) (MIC=12.5 μM), the peptide-resistant mutant is relatively resistant (MIC=50 μM). Note that the MIC values for (d) and (e) against *E. coli* Cl-Pep$^R$ (100 and 50 μM, respectively) are quite similar.

The activity of (e) against *E. coli* strains JSR-O (pBR322) and Ceph$^R$, *S. aureus* strains, *H. influenzae* 487 and Corynebacterium JK is of special interest; all of these are beta-lactam-resistant organisms. The basis of resistance to cephalothin in *E. coli* Ceph$^R$ and in Corynebacterium JK strains has not been elucidated. But *E. coli* pBR322 contains the TEM beta-lactamase, and *S. aureus* Pen$^R$ strains and *H. influenzae* 487 are also lactamase producers. The susceptibility of these strains to (e) is in accord with speculation that the efficacy of the haloalanyl cephem ester in lactamase-producing microorganisms will result from enzymatic release of a C-10 appended toxophore. On the other hand, note that both beta-lactam-resistant and -sensitive *S. epidermidis* (1239 P$^R$M$^R$ and M-1554 P$^S$M$^S$) strains are exquisitely sensitive to all of the cephems, as well as to the peptide (f).

Enzymatic Studies with Compounds of the Invention

Kinetic Constants for the Reactions of *E. coli* TEM beta-Lactamase with Cephalothin and the Cephalosporin Peptide Esters 7 and 17.

The peptide cephem esters 7 and 17 were both found to be substrates for the *E. coli* TEM beta-lactamase. The kinetic data for enzymatic turnover of these compounds, together with comparative figures for hydrolysis of cephalothin (1), reveal that the V$_{max}$ rates for reaction of the two peptidyl cephem esters are substantially greater than that obtained for cephalothin. Insofar as values for K$_M$ approximate those for K$_S$, it appears that the C$_{10}$-dipeptidyl substituents of 7 and 17 do not compromise the binding of the cephalosporin nucleus to the lactamase.

Having now fully described this invention it will be appreciated by those of ordinary skill in the art that the same can be performed within a variety of structures, parameters, compositions, modes of administration, and is applicable to a wide variety of bacteria, infectious diseases and the like. All of these are considered to be equivalent as they would not depart from the spirit or scope of the invention as claimed.

What is claimed is:

1. Cephalosporin compounds of the Formula (I):

$$\text{(structure with } R^1, S, N, COOW, CH_2-Y(-X)_{\overline{n}}Z\text{)} \quad (I)$$

wherein
W is a pharmaceutically acceptable salt or a carboxyl-protecting group;

n is an integer from 1 to 2;
—X— is —X¹— where
the X¹ moieties are the same or different and selected from the group consisting of (D) or (L)

Z is Z¹;
Y is —O—;
R¹ is selected from the group consisting of

R² is —CH₂R⁴, —CHR⁵₂ or —CR⁵₃;

where R⁴ is F, Cl, Br, —OH, —CN, wherein Q¹, Q², and Q³ are the same or different and selected from the group consisting of H, F, Cl, or Br;
R⁵ is F, Cl, or Br; and Z¹ is H or an amino protecting group.

2. The compounds of claim 1 having the formula

3. The compounds of claim 1, wherein all moieties —X¹— are of the L configuration.
4. The compounds of claim 1, wherein R⁴ is halogen.
5. The compounds of claim 4, wherein R⁴ is chloro.
6. The compounds of claim 1, wherein R¹ is 7. A compound of claim 1 which is or pharmaceutically acceptable salts or esters thereof.

8. A compound of claim 1 which is or pharmaceutically acceptable salts or esters thereof.

9. A compound of claim 1 which is or pharmaceutically acceptable salts or esters thereof.

10. A composition useful for the treatment of bacterial infections which comprises an effective amount of a compound of claim 1 together with a pharmaceutically acceptable carrier.

11. A method of suppressing the growth of susceptible bacteria which comprises contacting said bacteria with an effective amount of the compound of claim 1.

* * * * *